(12) United States Patent
Goldman

(10) Patent No.: US 7,785,882 B2
(45) Date of Patent: Aug. 31, 2010

(54) NEURONAL PROGENITOR CELLS FROM HIPPOCAMPAL TISSUE AND A METHOD FOR ISOLATING AND PURIFYING THEM

(75) Inventor: Steven A. Goldman, South Salem, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 550 days.

(21) Appl. No.: 10/181,329

(22) PCT Filed: Jan. 18, 2001

(86) PCT No.: PCT/US01/01780

§ 371 (c)(1),
(2), (4) Date: Oct. 23, 2002

(87) PCT Pub. No.: WO01/53503

PCT Pub. Date: Jul. 26, 2001

(65) Prior Publication Data

US 2003/0211087 A1 Nov. 13, 2003

Related U.S. Application Data

(60) Provisional application No. 60/176,677, filed on Jan. 18, 2000.

(51) Int. Cl.
C12N 5/00 (2006.01)
C12N 5/02 (2006.01)
C12N 5/10 (2006.01)
C12N 5/071 (2010.01)
C12N 15/00 (2006.01)

(52) U.S. Cl. .................. 435/368; 435/325; 435/363; 435/366; 435/440

(58) Field of Classification Search .............. 435/325, 435/352, 354, 363, 366, 368
See application file for complete search history.

(56) References Cited

U.S. PATENT DOCUMENTS

| | | | |
|---|---|---|---|
| 5,654,189 A | 8/1997 | Lee et al. | |
| 5,661,032 A | 8/1997 | Miller et al. | |
| 5,750,376 A | 5/1998 | Weiss et al. | |
| 5,753,505 A | 5/1998 | Luskin | |
| 5,753,506 A * | 5/1998 | Johe | 435/377 |
| 5,770,414 A | 6/1998 | Gage et al. | |
| 5,780,300 A | 7/1998 | Artavanis-Tsakonas et al. | |
| 5,830,651 A | 11/1998 | Cauley et al. | |
| 5,837,535 A | 11/1998 | Joseph et al. | |
| 5,980,885 A | 11/1999 | Weiss et al. | |
| 6,000,772 A | 12/1999 | Miller et al. | |
| 6,245,564 B1 | 6/2001 | Goldman et al. | |
| 6,812,027 B2 | 11/2004 | Goldman et al. | |

2004/0029269 A1 2/2004 Goldman et al.

FOREIGN PATENT DOCUMENTS

| | | |
|---|---|---|
| WO | WO 93/01275 | 1/1993 |
| WO | WO 94/02593 | 2/1994 |
| WO | WO 94/09119 | 4/1994 |
| WO | WO 96/38576 | 12/1996 |
| WO | WO 97/07200 | 2/1997 |
| WO | WO 99/49014 | 9/1999 |
| WO | WO 00/23571 | 4/2000 |
| WO | WO 01/46384 | 6/2001 |
| WO | WO 03/014320 | 2/2003 |

OTHER PUBLICATIONS

Altman et al., "Autoradiographic and Histological Evidence of Postnatal Hippocampal Neurogenesis in Rats," *J. Comp. Neur.* 124:319-336 (1965).

Antel et al., "Neuronal Progenitors—Learning from the Hippocampus," *Nat. Med.* 6(3):249-250 (2000).

Barami et al., "Hu Protein as an Early Marker of Neuronal Phenotypic Differentiation by Subependymal Zone Cells of the Adult Songbird Forebrain," *J. Neurobiol.* 28:82-101 (1995).

Barnea et al., "Seasonal Recruitment of Hippocampal Neurons in Adult Free-Ranging Black-Capped Chickadees," *Proc. Natl. Acad. Sci. USA* 91:11217-11221 (1994).

Bayer et al., "Neurons in the Rat Dentate Gyrus Granular Layer Substantially Increase During Juvenile and Adult Life," *Science* 216:890-892 (1982).

(Continued)

*Primary Examiner*—Anne-Marie Falk
(74) *Attorney, Agent, or Firm*—Nixon Peabody LLP

(57) ABSTRACT

The present invention relates to an enriched or purified preparation of isolated hippocampal neural progenitor cells and progeny thereof. The present invention also relates to a method of separating neural progenitor cells from a mixed population of cell types from hippocampal tissue. This method includes selecting a promoter which functions selectively in the neural progenitor cells, introducing a nucleic acid molecule encoding a fluorescent protein under control of said promoter into all cell types of the mixed population of cell types from hippocampal tissue, allowing only the neural progenitor cells, but not other cell types, within the mixed population to express said fluorescent protein, identifying cells of the mixed population of cell types that are fluorescent, which are restricted to the neural progenitor cells, and separating the fluorescent cells from the mixed population of cell types, wherein the separated cells are restricted to the neural progenitor cells.

6 Claims, 10 Drawing Sheets

OTHER PUBLICATIONS

Counter et al., "Telomere Shortening Associated with Chromosome Instability is Arrested in Immortal Cells Which Express Telomerase Activity," *EMBO Journal* 11(5):1921-1929 (1992).

"CytoTherapeutics' Researchers First to Directly Isolate Normal Human Neural Stem Cells," BW Health Wire News Release (Nov. 2, 1999), Reprint from Yahoo! Finance (Date Unknown).

Eriksson et al., "Neurogenesis in the Adult Human Hippocampus," *Nat. Med.* 4(11):1313-1317 (1998).

Gage et al., "Isolation, Characterization, and Use of Stem Cells from the CNS," *Annu. Rev. Neurosci.* 18:159-192 (1995).

Gage et al., "Survival and Differentiation of Adult Neuronal Progenitor Cells Transplanted to the Adult Brain," *Proc. Natl. Acad. Sci. USA* 92:11879-11883 (1995).

Galiana et al., "Proliferation and Differentiation Properties of Bipotent Glial Progenitor Lines Immortalized with the Adenovirus E1A Gene," *J. Neurosci. Res.* 36:133-146 (1993).

Goldman et al., "Human Neural Progenitor Cells: Better Blue than Green?" *Nat. Med.* 6(5):483-484 (2000).

Goldman et al., "Strategies Utilized by Migrating Neurons of the Postnatal Vertebrate Forebrain," *Trends Neurosci.* 21(3):107-114 (1998).

Gould et al., "Adrenal Hormones Suppress Cell Division in the Adult Rat Dentate Gyrus," *J. Neurosci.* 12(9)3642-3650 (1992).

Gould et al., "Learning Enhances Adult Neurogenesis in the Hippocampal Formation," *Nat. Neurosci.* 2(3):260-265 (1999).

Gould et al., "Neurogenesis in the Dentate Gyrus of the Adult Tree Shrew is Regulated by Psychosocial Stress and NMDA Receptor Activation," *J. Neurosci.* 17(7):2492-2498 (1997).

Gould et al., "Proliferation of Granule Cell Precursors in the Dentate Gyrus of Adult Monkeys is Diminished by Stress," *Proc. Natl. Acad. Sci. USA* 95:3168-3171 (1998).

Grinspan et al., "Platelet-Derived Growth Factor Is a Survival Factor for PSA-NCAM+ Oligodendrocyte Pre-Progenitor Cells," *J. Neurosci. Res.* 41:540-551 (1995).

Hohaus et al., "Telomerase Activity in Human Hematopoietic Progenitor Cells," *Haematologica* 82:262-268 (1997).

Hoshimaru et al., "Differentiation of the Immortalized Adult Neuronal Progenitor Cell Line HC2S2 into Neurons by Regulatable Suppression of the v-*myc* Oncogene," *Proc. Natl. Acad. Sci. USA* 93:1518-1523 (1996).

Kempermann et al., "More Hippocampal Neurons in Adult Mice Living in an Enriched Environment," *Nature* 386:493-495 (1997).

Kempermann et al., "New Nerve Cells for the Adult Brain. Adult Neurogenesis and Stem Cell Concept in Neurological Research," *Der Nervenartz* 69:851-857 (1998).

Kornack et al., "Continuation of Neurogenesis in the Hippocampus of the Adult Macaque Monkey," *Proc. Natl. Acad. Sci. USA* 96:5768-5773 (1999).

Kukekov et al., "Multipotent Stem/Progenitor Cells with Similar Properties Arise from Two Neurogenic Regions of Adult Human Brain," *Experimental Neurology* 156:333-344 (1999).

Martinez-Serrano et al., "Human Neural Progenitor Cells: Better Blue than Green?" *Nat. Med.* 6(5):483-484 (2000).

Mattson et al., "Intrinsic Factors in the Selective Vulnerability of Hippocampal Pyramidal Neurons," *Alzheimer's Disease and Related Disorders* 317:333-351 (1989).

Ohtsuka et al., "Regulated Expression of Neurogenic Basic Helix-Loop-Helix Transcription Factors During Differentiation of the Immortalized Neuronal Progenitor Cell Line HC2S2 into Neurons," *Cell Tissue Res.* 293:23-29 (1998).

Palmer et al., "The Adult Rat Hippocampus Contains Primordial Neural Stem Cells," *Mol. Cell Neurosci.* 8:389-404 (1997).

Pincus et al., "Fibroblast Growth Factor-2/Brain-Derived Neurotrophic Factor-Associated Maturation of New Neurons Generated from Adult Human Subependymal Cells," *Annals of Neurology* 43:576-585 (1998).

Ray et al., "Proliferation, Differentiation, and Long-term Culture of Primary Hippocampal Neurons," *Proc. Natl. Acad. Sci. USA* 90:3602-3606 (1993).

Raymon et al., "Immortalized Human Dorsal Root Ganglion Cells Differentiate into Neurons with Nociceptive Properties," *J. Neurosci.* 19:5420-5428 (1999).

Reynolds et al., "Generation of Neurons and Astrocytes from Isolated Cells of the Adult Mammalian Central Nervous System," *Science* 255:1707-1710 (1992).

Roy et al., "Identification, Isolation, and Promoter-Defined Separation of Mitotic Oligodendrocyte Progenitor Cells from the Adult Human Subcortical White Matter," *J. Neurosci.* 19(22):9986-9995 (1999).

Roy et al., "In Vitro Neurogenesis by Progenitor Cells Isolated from the Adult Human Hippocampus," *Nat. Med.* 6(3):271-277 (2000).

Scherer et al., "Differential Regulation of the 2',3'-Cyclic Nucleotide 3'-Phosphodiesterase Gene During Oligodendrocyte Development," *Neuron* 12:1363-1375 (1994).

Sharma et al., "Differentiation of Immortal Cells Inhibits Telomerase Activity," *Proc. Natl. Acad. Sci. USA* 92:12343-12346 (1995).

Suhonen et al., "Differentiation of Adult Hippocampus-Derived Progenitors into Olfactory Neurons In Vivo," *Nature* 383:624-627 (1996).

Tse et al., "Voltage-Activated $K^+$ Currents in Acutely Isolated Hippocampal Astrocytes," *J. Neurosci.* 12(5):1781-1788 (1992).

van Praag et al., "Running Increases Cell Proliferation and Neurogenesis in the Adult Mouse Dentate Gyrus," *Nat. Neurosci.* 2(3):266-270 (1999).

Wang et al., "Isolation of Neuronal Precursors by Sorting Embryonic Forebrain Transfected with GFP Regulated by the $T\alpha 1$ Tubulin Promoter," *Nat. Biotech.* 16:196-201 (1998).

Weiss et al., "Is There a Neural Stem Cell in the Mammalian Forebrain?" *Trends Neurosci.* 19(9):387-393 (1996).

Roy et al., "Promoter-Targeted Selection and Isolation of Neural Progenitor Cells From the Adult Human Ventricular Zone," Journal of Neuroscience Research 59:321-331 (2000).

* cited by examiner

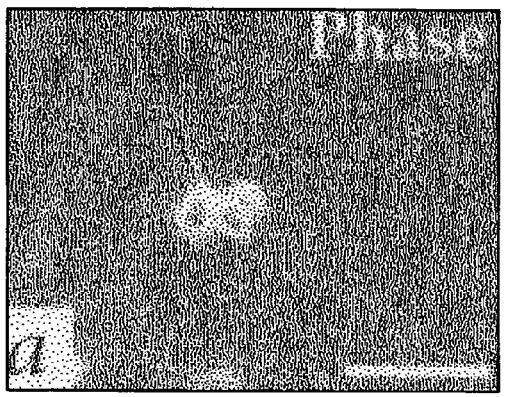 
FIG. 3A	FIG. 3B
 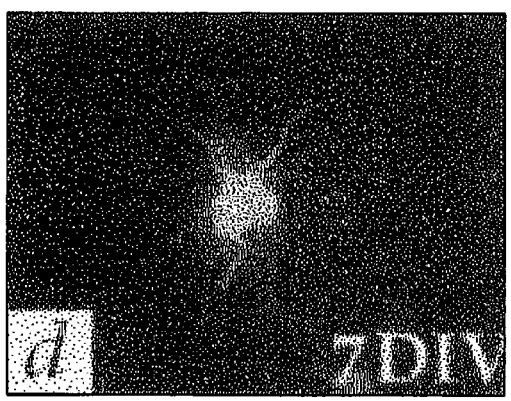
FIG. 3C	FIG. 3D
 
FIG. 3E	FIG. 3F

  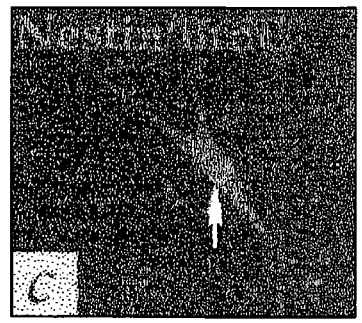
FIG. 4A     FIG. 4B     FIG. 4C
 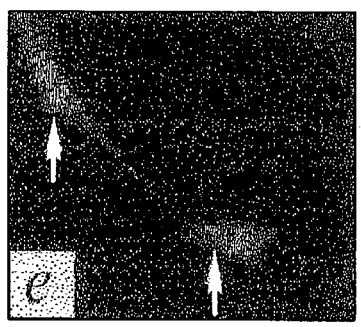 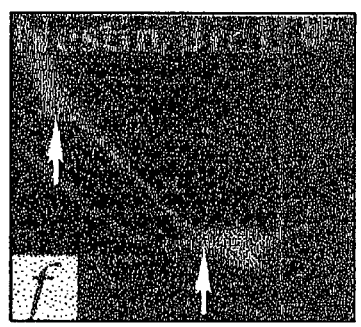
FIG. 4D     FIG. 4E     FIG. 4F
 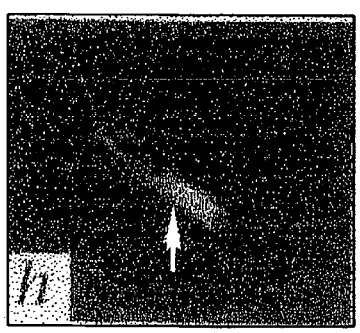 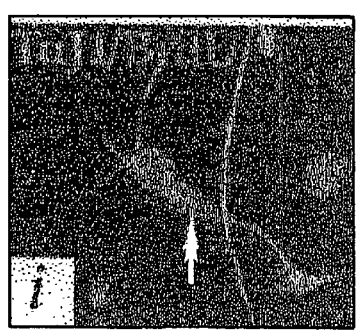
FIG. 4G     FIG. 4H     FIG. 4I

NEURONAL PROGENITOR CELLS FROM HIPPOCAMPAL TISSUE AND A METHOD FOR ISOLATING AND PURIFYING THEM

This application claims the benefit of U.S. Provisional Patent Application Serial No. 60/176,677, filed Jan. 18, 2000, which is hereby incorporated by reference.

The subject matter of this application was made with support from the United States Government under grants RO1 NS29813 and RO1 NS33106 of the National Institutes of Health.

FIELD OF THE INVENTION

The present invention relates generally to hippocampal neural progenitor cells and a method of separating cells of interest, in particular neural progenitor cells, from hippocampal tissue.

BACKGROUND OF THE INVENTION

Throughout this application various publications are referenced, many in parenthesis. Full citations for these publications are provided at the end of the Detailed Description. The disclosures of these publications in their entireties are hereby incorporated by reference in this application.

The damaged brain is largely incapable of functionally significant structural self-repair. This is due in part to the apparent failure of the mature brain to generate new neurons (Korr, 1980; Sturrock, 1982). However, the absence of neuronal production in the adult vertebrate forebrain appears to reflect not a lack of appropriate neuronal precursors, but rather their tonic inhibition and/or lack of post-mitotic trophic and migratory support. Converging lines of evidence now support the contention that neuronal and glial precursor cells are distributed widely throughout the ventricular subependymal of the adult vertebrate forebrain, persisting across a wide range of species groups (Goldman and Nottebohm, 1983; Reynolds and Weiss, 1992; Richards et al., 1992; Kirschenbaum et al., 1994; Kirschenbaum and Goldman, 1995a; reviewed in Goldman, 1995; Goldman, 1997; Goldman, 1998; Goldman and Luskin, 1998; and Gage et al., 1995). Most studies have found that the principal source of these precursors is the ventricular zone (Goldman and Nottebohm, 1983; Goldman, 1990; Goldman et al., 1992; Lois and Alvarez-Buylla, 1993; Morshead et al., 1994; Kirschenbaum et al., 1994; Kirschenbaum and Goldman, 1995), though competent neural precursors have been obtained from parenchymal sites as well (Richards et al., 1992; Palmer et al., 1995; Pincus et al., 1998). In general, adult progenitors respond to epidermal growth factor (EGF) and basic fibroblast growth factor (bFGF) with proliferative expansion (Reynolds and Weiss, 1992; Kilpatrick and Bartlett, 1995; Kuhn et al., 1997), may be multipotential (Vescovi et al., 1993; Goldman et al., 1996), and persist throughout life (Goldman et al., 1996). In rodents and humans, their neuronal daughter cells can be supported by brain-derived neurotrophic factor (BDNF) (Kirschenbaum and Goldman, 1995a), and become fully functional in vitro (Kirschenbaum et al., 1994, Pincus et al., 1998a, and Pincus et al. 1998b), like their avian counterparts (Goldman and Nedergaard, 1992).

A major impediment to both the analysis of the biology of adult neural precursors, and to their use in engraftment and transplantation studies, has been their relative scarcity in adult brain tissue, and their consequent low yield when harvested by enzymatic dissociation and purification techniques. As a result, attempts at either manipulating single adult-derived precursors or enriching them for therapeutic replacement have been difficult. The few reported successes at harvesting these cells from dissociates of adult brain, whether using avian (Goldman et al., 1992; 1996), murine (Reynolds and Weiss, 1992), or human (Kirschenbaum et al., 1994) tissue, have all reported less than 1% cell survival. Thus, several groups have taken the approach of raising lines derived from single isolated precursors, continuously exposed to mitogens in serum-free suspension culture (Reynolds and Weiss, 1992; Morshead et al., 1994; Palmer et al., 1995). As a result, however, many of the basic studies of differentiation and growth control in the neural precursor population have been based upon small numbers of founder cells, passaged greatly over prolonged periods of time, under constant mitogenic stimulation. The phenotypic potential, transformation state, and karyotype of these cells are all uncertain; after repetitive passage, it is unclear whether such precursor lines remain biologically representative of their parental precursors, or instead become transformants with perturbed growth and lineage control.

In order to devise a more efficient means of isolating native, unpassaged and untransformed progenitor cells from brain tissue, a strategy by which brain cells could be freely dissociated from brain tissue, then transduced in vitro with plasmid DNA bearing a fluorescent reporter gene under the control of neural progenitor cell-type specific promoters was developed (Wang et al., 1998). This permitted isolation of the elusive neuronal progenitor cell of the CNS, using the Tα1 tubulin promoter, a regulatory sequence expressed only in neuronal progenitor cells and young neurons.

Neuronal progenitor cells in the ventricular lining and dentate gyrus of the adult mammalian hippocampus are integral to learning, and to the acquisition and storage of new memories. Most dementing illnesses, including Alzheimer's and Parkinson's disease, involve the loss of either these cells or other hippocampal cells to which they connect; in addition, many epileptic syndromes involve the loss of these cells, including epilepsies that arise from brain trauma, birth injury, hypoxic injury, and some infections. Thus, a wide variety of neurological diseases share as a common feature damage to, or loss of, the hippocampal dentate cell population.

However, hippocampal progenitor cells have never been isolated. The existence of these hippocampal progenitor cells has been reported in adult animals ranging from chickadees to humans (Altman et al., 1965; Kaplan et al., 1977; Bayer et al., 1982; Barnea et al., 1994; Gould et al., 1997; Gould et al., 1998; Eriksson et al., 1998). In rodents, hippocampal neurogenesis can be modulated by stress (Gould et al., 1992), enrichment (Kempermann et al., 1997), exercise (van Praag et al., 1999), and learning (Gould et al., 1999). Among primates, both adult macaques (Gould et al., 1998; Kornack et al., 1999) and humans (Eriksson et al., 1998) exhibit histological evidence of neurogenesis in the dentate gyrus. Hippocampal cells have been found in suspension cultures derived from both adult rats (Palmer et al., 1997) and humans (Kukekov et al., 1999); these can expand in response to FGF2, include multipotential founders (Palmer et al., 1997), and are capable of heterotopic integration into other regions of granular neurogenesis, such as the olfactory subependyma (Suhonen et al., 1996). Yet despite the widespread incidence of hippocampal neurogenesis in adult animals, native hippocampal progenitor cells have never been separated and purified as such, in rodents or humans. As a result, no assessment of the abundance, factor-responsiveness, or regenerative capacity of these cells has been possible.

A strong need therefore exists for a new strategy for identifying, separating, isolating, and purifying native neural progenitor cells from hippocampal tissue.

SUMMARY OF THE INVENTION

The subject invention relates to an enriched or purified preparation of isolated hippocampal neural progenitor cells and progeny thereof.

The present invention also relates to a method of separating neural progenitor cells from a mixed population of cell types from hippocampal tissue, based upon cell-type selective expression of cell-specific promoters. This method includes selecting a promoter which functions selectively in the neural progenitor cells and introducing a nucleic acid molecule encoding a fluorescent protein under control of said promoter into all cell types of the mixed population of cell types derived from hippocampal tissue of both fetal and adult origin. Only the neural progenitor cells, but not other cell types, within the mixed population are allowed to express the fluorescent protein. Cells of the mixed population of cell types that are fluorescent, which are restricted to the neural progenitor cells, are identified and the fluorescent cells are separated from the mixed population of cell types. As a result, the separated cells are restricted to the neural progenitor cells.

A promoter is chosen which specifically drives expression in neural progenitor cells but not in other cells of the hippocampal tissue. The fluorescent protein will therefore only be expressed and detectable in cells in which the promoter operates, i.e. in those cells for which the transcriptional activity of that promoter is specific.

The method involves the introduction of a nucleic acid encoding the fluorescent protein, under the control of the cell specific promoter, into a plurality of cells. Various methods of introduction known to those of ordinary skill in the art can be utilized, including (but not limited to) viral mediated transformation (e.g., adenovirus mediated transformation), electroporation, and liposomal mediated transformation.

After cell specific expression of the fluorescent protein, such as green fluorescent protein (GFP), the cells expressing the fluorescent protein are separated by an appropriate means. In particular, the cells can be separated by fluorescence activated cell sorting. The method of the subject invention thus provides for the enrichment and separation of the hippocampal neural progenitor cells.

Contemporary approaches toward the use of neural progenitor cells have focused upon preparing clonal lines derived from single progenitors. However, such propagated lines can become progressively less representative of their parental precursors with time and passage in vitro. To circumvent these difficulties, the method of the subject invention provides a strategy for the live cell identification, isolation and enrichment of native hippocampal neural progenitor cells, by fluorescence-activated cell sorting of human hippocampal cells transfected with fluorescent protein, driven by the neural progenitor cell-specific Tα1 tubulin promoter or nestin enhancer. Using this approach, hippocampal neural progenitor cells can be identified and selectively harvested from a wide variety of samples, including embryonic and adult brain of avian, mammalian, and human origin. This approach allows for the enrichment of neural precursors from fetuses or adults, with a yield substantially higher than that achievable through standard techniques of selective dissection and differential centrifugation. Tα1, a member of the α-tubulin multigene family, is localized almost exclusively to the nervous system, within which it appears specific for neurons (Miller et al., 1987; Gloster et al., 1994). Though most abundant in young neurons extending neurites, it is first expressed earlier in neuronal ontogeny, including in ventricular zone cells (Miller et al., 1987). Nestin is an intermediate filament expressed by neural stem and progenitor cells; the second intronic enhancer of nestin directs its transcription to neural progenitor cells of the fetal neuroepithelium (Lothian et al., 1997). As a result, the Tα1 tubulin promoter and the nestin enhancer were chosen for their ability to target transgene expression to hippocampal neural progenitor cells.

Extension of this approach to include fluorescent transgenes under the control of stage- and phenotype-specific promoters (both of which are intended to be covered by reference to "cell-specific" promoters herein) allows even more specific separations to be performed, for example, of hippocampal neural progenitors over a range of developmental stages. This strategy permits sufficient enrichment for in vivo implantation of the defined and separated progenitor pools, as well as for in vitro analyses of phenotypic specification and growth control.

By providing a means of identifying hippocampal neural progenitor cells while alive, even when present in small numbers in mixed populations, the use of fluorescent transgenes driven by cell type-selective promoters such as the Tα1 tubulin promoter and the nestin enhancer will allow the specification of phenotype to be studied and perturbed on the single cell level, an approach that had previously only been feasible on larger populations. Indeed, when used in conjunction with post-transfection fluorescence-activated cell sorting (FACS), this strategy may permit the enrichment and purification of any cell type for which stage- or phenotype-specific promoters are available.

The method of the present invention provides a new strategy for the isolation and purification of hippocampal neural progenitor cells, from the adult brain. These cells may be used in both basic analyses of precursor and stem cell growth control, as well as in more applied studies of their transplantability and engraftment characteristics. Generally, by providing a means to identify and enrich neural precursor cells from adult brain, this strategy may allow a significant acceleration in the study of precursor and stem cell biology, as well as providing native unpassaged adult precursor cells in sufficient number for implantation studies. As such, this approach may spur the development of induced adult neurogenesis as a viable therapeutic modality for the structural repair of the damaged central nervous system.

BRIEF DESCRIPTION OF THE DRAWINGS

These and other features and advantages of this invention will be evident from the following detailed description of preferred embodiments when read in conjunction with the accompanying drawings in which:

FIGS. 2A-B show a monolayer dissociate of adult human dentate gyrus, removed from a 33 year-old man after temporal lobectomy. FIGS. 2A-B show phase and fluorescence images at 7 days in vitro (DIV) of a cluster of adult dentate neurons, labeled with the anti-neuronal antibody MAP-2 (FIG. 2B). FIG. 2C shows a hippocampal culture derived from a 35 year-old, immunostained for βIII-tubulin. This culture was exposed to BrdU in vitro, then fixed and stained for BrdU as well as βIII-tubulin.

FIGS. 2D-F show TuJ1⁺/BrdU⁺ neurons, generated by mitotic neurogenesis from hippocampal progenitors. Scale: 30 μm.

FIGS. 3A-F show hippocampal cultures derived from a 63 year-old man that were transfected at 5 days in vitro CDIV with pPTα1:hGFP, to identify neuronal precursor cells and their young neuronal daughters. p/Tα1:hGFP⁺ cells were photographed at 7 (FIGS. 3A-D) and 14 (FIGS. 3E-F) days in vitro after transfection. FIGS. 3A, C, and E are phase contrast images. FIGS. 3B, D, and F are fluorescence images. Scale=30 μm.

FIGS. 4A-I show phase contrast (FIGS. 4A, D, and G) and fluorescence (FIGS. 4B, E, and H) images of E/nestin:EGFP⁺ hippocampal cells. FIGS. 4C and F show expressed human nestin protein, while FIG. 4I, in a matched culture, shows immunostaining for βIII-tubulin. All 3 cells had incorporated BrdU during their first week in culture, and were fixed at 7 DIV.

FIGS. 5A-D show the P/Tα1:hGFP-based sort graphs obtained from dentate gyri derived from 5 (FIGS. 5A-B) and 20 year-old (FIGS. 5 C-D) male patients. The cells were transfected with either P/Tα1:lacZ (FIGS. 5A and C, a non-fluorescent control), or pP/Tα1:hGFP (FIGS. 5B and D). For both sorts, GFP fluorescence intensity (FL1) was plotted against cell size (forward scatter, FCS). An average of 1.36% and 1.69% of the cells derived from the 5 and 20 year-old patients, respectively, achieved an arbitrary threshold of P/Tα1:hGFP fluorescence intensity, which was calibrated to that achieved by 0.03% of control cells. FIGS. 5E-H show the sort results obtained after transfecting dentate gyrus cultures of the 5 year-old with either P/CMV:lacZ (a non-fluorescent control) (FIG. 5E) or E/nestin:EGFP (FIG. 5F). For each sort, GFP fluorescence intensity (FL1) was plotted against cell size (forward scatter, FCS). In this typical example, 1.69% of the E/nestin:EGFP-sorted cells achieved threshold fluorescence, which was calibrated to that achieved by 0.01% of control cells. FIGS. 5G-H show low power phase (FIG. 5G) and fluorescent (FIG. 5H) micrographs of the E/nestin:EGFP⁺ cells of the plot of FIG. 5F, 2 hours after FACS. Most sorted cells visibly expressed GFP.

In FIG. 6A, the cells were transfected with E/nestin:EGFP, fixed 4 days later, and co-stained for neuronal βIII tubulin. In FIG. 6B, the culture was sorted, and the E/nestin:EGFP⁺ cells allowed to differentiate in 5% FBS, then fixed and stained for βIII tubulin 3 days after FACS. In FIGS. 6C-D, hippocampal cells from this patient were transfected with P/Tα1:hGFP and stained for βIII-tubulin (FIG. 6C: unsorted, at 4 days in vitro; FIG. 6D: a week after FACS, total 14 days in vitro). The P/Tα1:GFP⁺ cells expressed MAP2 as well as βIII-tubulin, and incorporated BrdU during the first 7 days in vitro. Scale=30 μm.

FIGS. 8A-D show images of P/Tα1:hGFP-sorted cells loaded with the calcium indicator dye fluo-3, 10 days after FACS; these have matured uniformly into fiber-bearing cells of neuronal morphology. FIG. 8B shows the same field as in FIG. 8A after exposure to glutamate. FIG. 8C shows the same field upon return to baseline after media wash. FIG. 8D shows the same field after exposure to a depolarizing stimulus of 60 mM KCl. The neurons displayed rapid, reversible, >300% elevations in cytosolic calcium in response to potassium, consistent with the activity of neuronal voltage-gated calcium channels. Scale=50 μm. FIG. 8E shows a representative cell 14 days after P/Tα1:hGFP-based FACS. Identified visually as a progenitor-derived neuron on the basis of its residual GFP expression, the cell was patch-clamped in a voltage-clamped configuration, and its responses to current injection recorded (see FIG. 8F). The fast negative deflections noted after current injection are typical of the voltage-gated sodium currents of mature neurons.

DETAILED DESCRIPTION OF THE INVENTION

Figure 1:
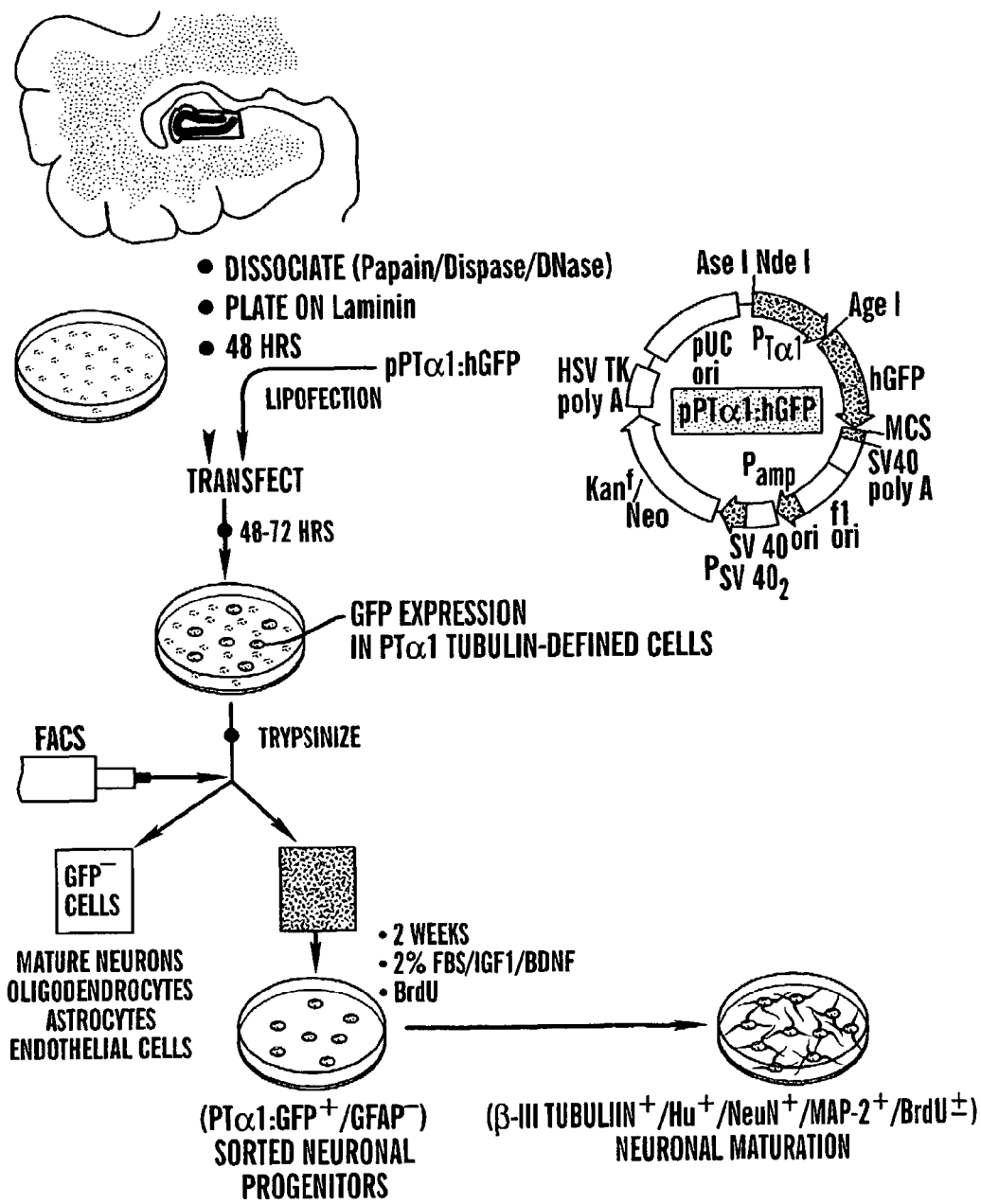
FIG. 1 shows a schematic outlining the strategy by which pPTα1:hGFP and E/nestin:EGFP-based fluorescence activated cell sorting (FACS) was used to extract neuronal progenitor cells from the adult human hippocampus.
Figure 2A:
FIGS. 2A-F show that the adult human hippocampus harbors mitotic neuronal progenitor cells.
Figure 2B:
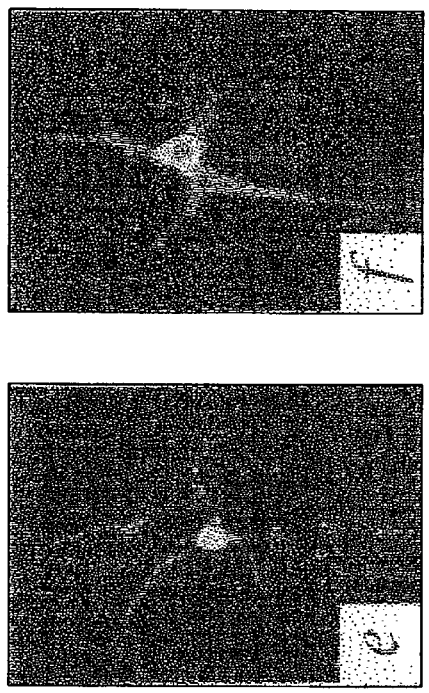
Figure 2F:
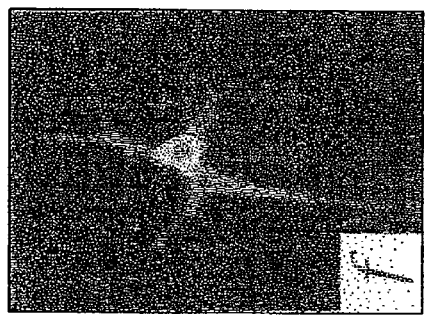
Figure 2E:
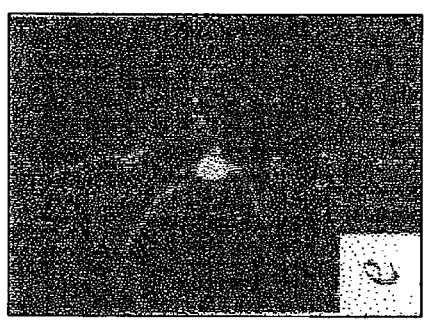
Figure 2D:
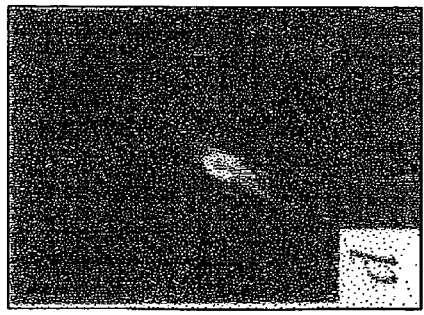
Figure 2C:
Figure 5A:
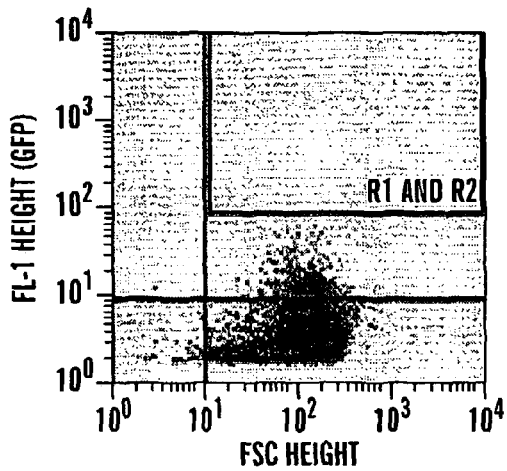
FIGS. 5A-H show that P/Tα1:hGFP and E/nestin:EGFP-identified neural progenitors can be isolated by FACS.
Figure 5B:
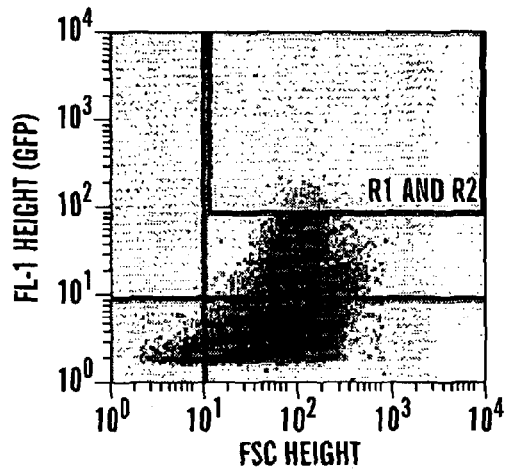
Figure 5C:
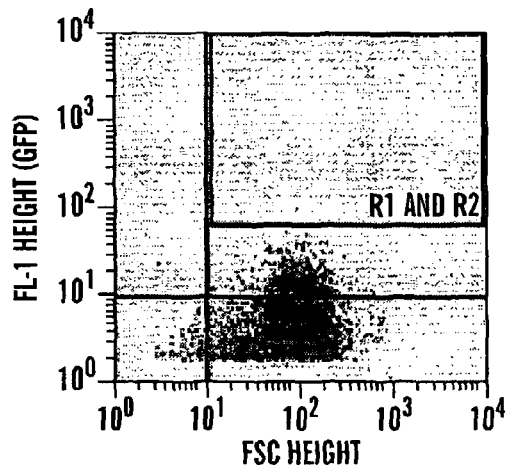
Figure 5D:
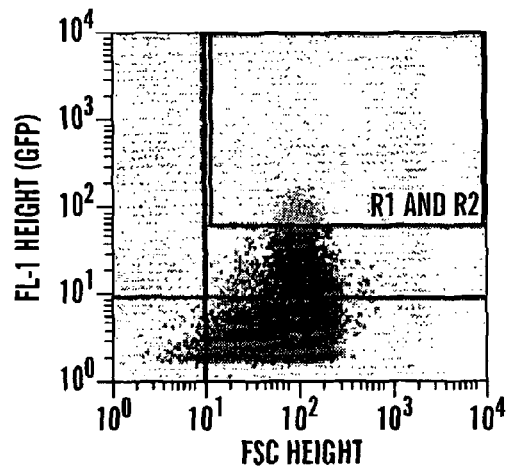
Figure 5E:
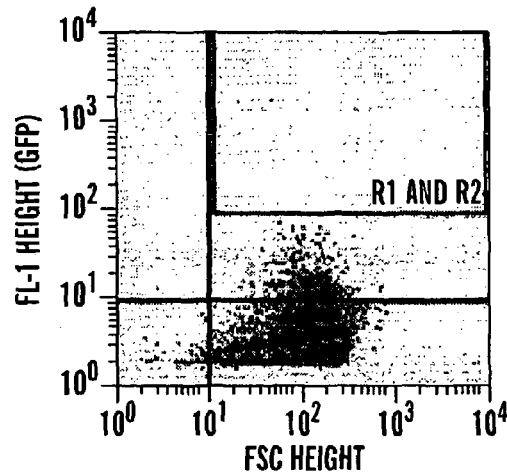
Figure 5F:
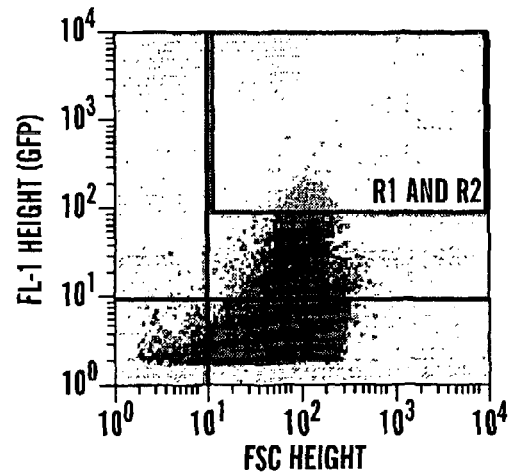
Figure 5G:
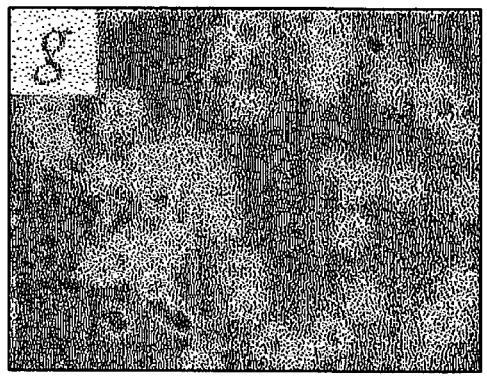
Figure 5H:
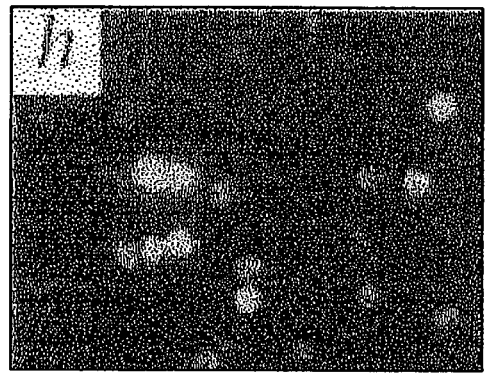
Figure 6A:
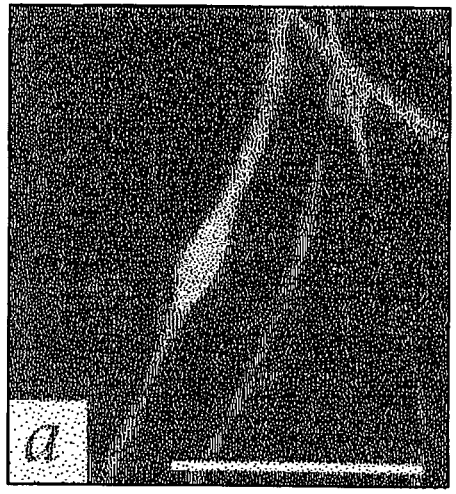
FIGS. 6A-D show cells derived from the dissociated dentate gyrus of a 20 year-old man.
Figure 6B:
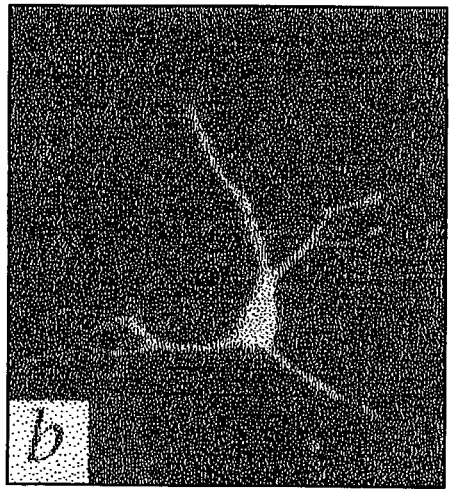
Figure 6C:
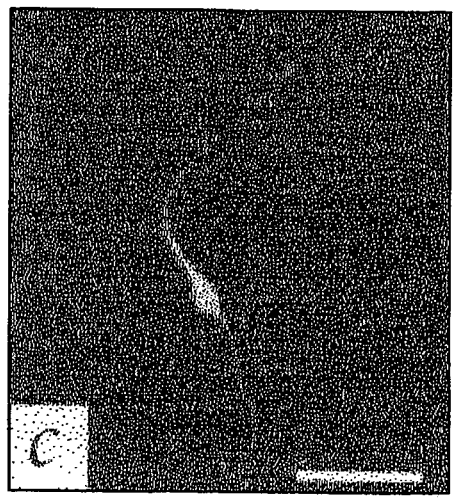
Figure 6D:
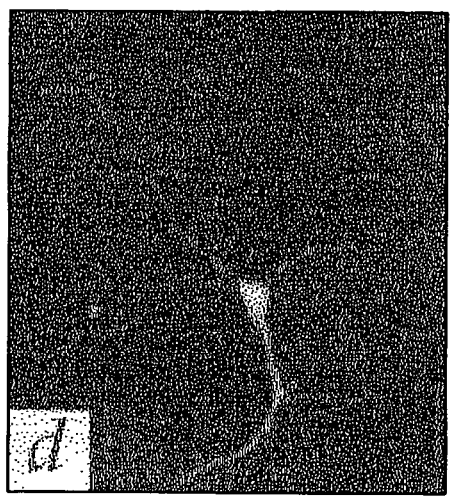

A plasmid designated pGFP10.1 has been deposited pursuant to, and in satisfaction of, the requirements of the Budapest Treaty on the International Recognition of the Deposit of Microorganisms for the Purposes of Patent Procedure, with the American Type Culture Collection (ATCC), 10801 University Boulevard, Manassas, Va. 20110-2209 under ATCC Accession No. 75547 on Sep. 1, 1993. This plasmid is commercially available from the ATCC due to the issuance of U.S. Pat. No. 5,491,084 on Feb. 13, 1996 in which the plasmid is described. This plasmid comprises a cDNA which encodes a green fluorescent protein (GFP) of *Aequorea Victoria* as disclosed in U.S. Pat. No. 5,491,084 to Chalfie et al., the contents of which are incorporated herein by reference.

The plasmid designated pTα1-hGFP has been deposited pursuant to, and in satisfaction of, the requirements of the Budapest Treaty on the International Recognition of the Deposit of Microorganisms for the Purposes of Patent Procedure, with the American Type Culture Collection (ATCC), 10801 University Boulevard, Manassas, Va. 20110-2209 under ATCC Accession No. 98299 on Jan. 21, 1997. This plasmid uses the humanized GFP (GFPh) of Zolotukhin and Muzyczka (Levy et al. 1996b), and the Tα1 promoter sequence provided by Dr. F. Miller (Montreal). In accordance with the subject invention, the Tα1 promoter can be replaced with another specific promoter, and the GFPh gene can be replaced with another form of GFP, by using standard restriction enzymes and ligation procedures.

A plasmid designated pE/nestin:EGFP has been deposited pursuant to, and in satisfaction of, the requirements of the Budapest Treaty on the International Recognition of the Deposit of Microorganisms for the Purposes of Patent Procedure, with the American Type Culture Collection (ATCC), 10801 University Boulevard, Manassas, Va. 20110-2209 under ATCC Accession No. PTA-2853 on Dec. 26, 2000.

As used herein, the term "isolated" when used in conjunction with a nucleic acid molecule refers to: 1) a nucleic acid molecule which has been separated from an organism in a substantially purified form (i.e. substantially free of other substances originating from that organism), or 2) a nucleic acid molecule having the same nucleotide sequence but not necessarily separated from the organism (i.e. synthesized or recombinantly produced nucleic acid molecules).

The subject invention provides an enriched or purified preparation of isolated hippocampal neural progenitor cells and progeny thereof.

Neuronal progenitor cells in the ventricular lining and dentate gyrus of the adult mammalian hippocampus are integral to learning, and to the acquisition and storage of new memories. Most dementing illnesses, including Alzheimer's and Parkinson's disease, involve the loss of either these cells or other hippocampal cells to which they connect; in addition, many epileptic syndromes involve the loss of these cells, including epilepsies that arise from brain trauma, birth injury, hypoxic injury, and some infections. Thus, a wide variety of neurological diseases share as a common feature damage to, or loss of, the hippocampal dentate cell population.

In one embodiment, the enriched or purified preparation of isolated hippocampal neural progenitor cells and progeny thereof according to the present invention are of mammalian and/or human origin.

In another embodiment, the enriched or purified preparation of isolated hippocampal neural progenitor cells and progeny thereof are from an adult or a fetus.

In yet another embodiment, the enriched or purified preparation of isolated hippocampal neural progenitor cells and progeny thereof give rise to dentate gyrus.

The enriched or purified preparation of isolated hippocampal neural progenitor cells and progeny thereof may be immortalized, for example, with a transforming oncogene.

The enriched or purified preparation of isolated hippocampal neural progenitor cells and progeny thereof may also be transduced with an exogenous transgene.

The native prospectively-identified and directly-harvested, non-transformed hippocampal neural progenitor cells according to the present invention divide in vitro, and give rise to antigenically typical, functionally appropriate neurons.

The cells of the present invention may be used in both basic analyses of precursor and stem cell growth control, as well as in directly applied studies of their transplantability and engraftment characteristics. The cells similarly can be used in support of the structural repair of the damaged central nervous system, such as in the damaged or degenerated adult hippocampus.

The subject invention also provides a method of separating neural progenitor cells from a mixed population of cell types from hippocampal tissue, based upon cell type-selective expression of cell specific promoters. This method includes selecting a promoter which functions selectively in the neural progenitor cells, introducing a nucleic acid molecule encoding a fluorescent protein under control of said promoter into all cell types of the mixed population of cell types from hippocampal tissue, allowing only the neural progenitor cells, but not other cell types, within the mixed population to express said fluorescent protein, identifying cells of the mixed population of cell types that are fluorescent, which are restricted to the neural progenitor cells, and separating the fluorescent cells from the mixed population of cell types, wherein the separated cells are restricted to the neural progenitor cells.

The cells of particular interest according to the subject invention are hippocampal neural progenitor cells. "Specific", as used herein to describe a promoter, means that the promoter functions only in the chosen cell type. A chosen cell type can refer to different stages in the developmental cycle of a cell.

The mixed population of cell types may be in tissue, i.e., hippocampal tissue, or in cell culture.

Illustrative promoters for hippocampal neural progenitor cells include a T$\alpha$1 tubulin promoter, a nestin enhancer, and a Sox2 promoter (Zappone et al., 2000).

Having determined the cell of interest and selected a promoter specific for the cell of interest, a nucleic acid molecule encoding a fluorescent protein, preferably a green fluorescent protein, under the control of the promoter is introduced into a plurality of cells to be sorted.

The isolated nucleic acid molecule encoding a green fluorescent protein can be deoxyribonucleic acid (DNA) or ribonucleic acid (RNA, including messenger RNA or mRNA), genomic or recombinant, biologically isolated or synthetic. The DNA molecule can be a cDNA molecule, which is a DNA copy of a messenger RNA (mRNA) encoding the GFP. In one embodiment, the GFP can be from *Aequorea victoria* (U.S. Pat. No. 5,491,084). A plasmid encoding the GFP of *Aequorea Victoria* is available from the ATCC as Accession No. 75547. Other mutated forms of this GFP including, but not limited to, pRSGFP, EGFP, and EYFP, among others, are commercially available from Clontech Laboratories, Inc. (Palo Alto, Calif.).

Mutated forms of GFP that emit more strongly than the native protein, as well as forms of GFP amenable to stable translation in higher vertebrates, are now available and can be used for the same purpose. The plasmid designated pT$\alpha$1-GFPh (ATCC Accession No. 98299) includes a humanized form of GFP. Indeed, any nucleic acid molecule encoding a fluorescent form of GFP can be used in accordance with the subject invention. Furthermore, any nucleic acid molecule encoding an enzyme that can catalyze the conversion of a fluorgenic substrate to a fluorophone can be used in accordance with the subject invention. An example is the use of a cell-specific promoter to drive lacZ expression, with the detection and sorting of lacZ-expressing cells being by means of incubation with the fluorgenic substrates FDG (fluorescein-$\beta$-D-galactopyranoside) or CMFDG (chloromethyl-FDG).

Standard techniques are then used to place the nucleic acid molecule encoding GFP under the control of the chosen cell specific promoter. Generally, this involves the use of restriction enzymes and ligation (see below).

The resulting construct, which comprises the nucleic acid molecule encoding the GFP under the control of the selected promoter (itself a nucleic acid molecule) (with other suitable regulatory elements if desired), is then introduced into a plurality of cells which are to be sorted. Techniques for introducing the nucleic acid molecules of the construct into the plurality of cells may involve the use of expression vectors which comprise the nucleic acid molecules. These expression vectors (such as plasmids and viruses) can then be used to introduce the nucleic acid molecules into the plurality of cells.

Various methods are known in the art for introducing nucleic acid molecules into host cells. These include: 1) microinjection, in which DNA is injected directly into the nucleus of cells through fine glass needles; 2) dextran incubation, in which DNA is incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. Some of the DNA evades destruction in the cytoplasm of the cell and escapes to the nucleus, where it can be transcribed into RNA like any other gene in the cell; 3) calcium phosphate coprecipitation, in which cells efficiently take in DNA in the form of a precipitate with calcium phosphate; 4) electroporation, in which cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures (passage through these vesicles may sometimes destroy or damage DNA); 5) liposomal mediated transformation, in which DNA is incorporated into artificial lipid vesicles, liposomes, which fuse with the cell membrane, delivering their contents directly into the cytoplasm; 6) biolistic transformation, in which DNA is absorbed to the surface of gold particles and fired into cells under high pressure using a ballistic device; and 7) viral-mediated transformation, in which nucleic acid molecules are introduced into cells using viral vectors. Since viral growth depends on the ability to get the viral genome into cells, viruses have devised efficient methods for doing so. These viruses include retroviruses and lentivirus, adenovirus, herpesvirus, and adeno-associated virus.

As indicated, some of these methods of transforming a cell require the use of an intermediate plasmid vector. U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture. The DNA sequences are cloned into the plasmid vector using standard cloning procedures known in the art, as described by Sambrook et al. (1989).

In accordance with one of the above-described methods, the nucleic acid molecule encoding the GFP is thus introduced into a plurality of cells. The promoter which controls expression of the GFP, however, only functions in the cell type of interest (i.e., hippocampal neural progenitor cells). Therefore, the GFP is only expressed in the cell type of interest. Since GFP is a fluorescent protein, the cells of interest can therefore be identified from among the plurality of cells by the fluorescence of the GFP.

Any suitable means of detecting the fluorescent cells can be used. The cells may be identified using epifluorescence optics, and can be physically picked up and isolated by mechanical devices such as Quixell (Stoelting, Inc., St. Louis, Mo.) or Laser Tweezers (Cell Robotics Inc., Albuquerque, N. Mex.). They can also be separated in bulk through fluorescence activated cell sorting, a method that effectively separates the fluorescent cells from the non-fluorescent cells (e.g., Wang et al., 1998).

The method of the subject invention thus provides for the isolation and enrichment of hippocampal neural progenitor cells from embryonic and adult brain of both rodent and human derivation. Specifically, fluorescence-activated cell sorting of human hippocampal cells transfected with green fluorescent protein driven by the Tα1 tubulin promoter or the nestin enhancer is provided. In particular, tissue samples from eight male patients, 5-63 years old, were obtained. Dissociates of dentate tissue were transfected with either an expression vector encoding GFP under the control of the Tα1 tubulin promoter (p/Tα1:hGFP), or with an expression vector encoding EGFP under the control of the nestin second intronic enhancer (E/nestin:EGFP). Following GFP expression, the GFP$^+$ cells were extracted by FACS. The resulting native prospectively-identified and directly-harvested, non-transformed hippocampal neural progenitor cells divide in vitro, and give rise to antigenically typical, functionally appropriate neurons (see FIG. 1).

EXAMPLES

Example 1

Materials and Methods

Adult Human Hippocampal Dissociation and Culture

Adult human brain tissue was obtained in the course of temporal lobectomy, as described (Pincus et al., 1998b; Kirschenbaum et al., 1994). The hippocampus was dissected free of the ventricular surface, and the dentate gyrus then dissected from the rest of the tissue. This sample was cut into pieces of roughly 2 mm on edge, rinsed twice with PIPES (120 mM NaCl, 5 mM KCl, 25 mM glucose, 20 mM PIPES), and dissociated in papain/DNase, as described (Roy et al., 1999; Doetsch et al., 1999). The dispersed cells were collected and rinsed with DMEM/F12/N2 containing 20% platelet-depleted FBS (PD-FBS, Cocalico, Reamstown, Pa.) to stop the enzymatic dissociation, and resuspended at $1\times10^7$ cells/ml in DMEM/F12/N2 with 2% PD-FBS and 10 ng/ml FGF-2 (Sigma, St. Louis, Mich.). The cells were plated at 0.1 ml/dish into 35 mm Falcon Primaria plates coated with laminin (2 µg/cm$^2$), at 37° C. in 5% $CO_2$. Four hours later, an additional 0.7 ml DMEM/F12/N2/2% PD-FBS and 10 ng/ml FGF2 were added to each plate.

BrdU Labeling and Immunocytochemistry

Cultures were exposed continuously to BrdU (10 µg/ml) beginning 1 day after plating. Cells were fixed with 4% paraformaldehyde after 7, 14, or 28 DIV. They were immunostained first for BrdU, and then for either nestin, βIII-tubulin, or MAP-2. βIII-tubulin was detected using monoclonal antibody TuJ1 (Dr. A. Frankfurter), and MAP-2 by a rabbit anti-MAP2 (Dr. S. Halpain), each as described (Menezes et al., 1994; Barami et al., 1995). Nestin was detected using rabbit anti-human nestin (1:1000; Dr. U. Lendahl), and detected using biotinylated anti-rabbit IgG (1:200) and Texas Red-avidin (Vector Laboratories, Burlingame, Calif.).

Construction of Plasmids P/Tα1:hGFP and E/nestin:EGFP

Expression vectors encoding GFP, placed under the control of either the Tα1 tubulin promoter or the nestin enhancer were constructed. First, humanized GFP (hGFP) (Levy et al., 1996) was placed under the control of the Tα1 tubulin promoter to yield pP/Tα1:hGFP as described (Wang et al., 1998b). Next, EGFP was placed under the control of the nestin enhancer to generate E/nestin:EGFP. To this end, the enhancer element of the 2nd intron of the rat nestin gene, spanning bases 1162 and 1798 (Lothian et al., 1997), was placed upstream of the minimum promoter of heat shock protein-68 (hsp68) (Rossant et al., 1991); the resultant E/nestin:P/hsp68 construct was ligated to EGFP-polyA (Clontech, Palo Alto, Calif.), to yield E/nestin:EGFP.

Transfection

The plasmid constructs were introduced into the cultured cells after 5-7 days in vitro by liposomal transfection, using lipofectin in Opti-MEM (Life Technologies) as described (Wang et al., 1998b). After a 6 hour transfection period, the reactions were terminated by adding 10% PD-FBS in DMEM/F12/N2. Two hours later, the cells were returned to serum-free DMEM/F12/N2 with 10 ng/ml basic fibroblast growth factor (bFGF). GFP was imaged using an Olympus IX70 microscope. Maximum GFP expression was noted 6-7 days after transfection, and the cells were sorted at that time.

The net transfection efficiency, with P/CMV:lacz as positive control, averaged 9.40±0.9% (n=40 fields in 4 plates, derived from 2 patients).

Flow Cytometry and Sorting

Flow cytometry and sorting of hGFP+ cells was performed on a FACS vantage (Becton-Dickinson, San Jose, Calif.). Cells were washed with $Ca^{2+}/Mg^{2+}$-free Hank's Balanced Salt Solution (HBSS), then dissociated in 0.05% trypsin-EDTA for 5 minutes at 37° C. The reaction was terminated by DMEM/F12/N2 with 10% FBS. The cells ($2\times10^6$/ml) were then analyzed by light forward and right-angle (side-) scatter, and for GFP fluorescence through a 510±20 nm bandpass filter, as they traversed the beam of a Coherent INNOVA Enterprise II Ion Laser (488 nm, 100 mw). Sorting was done using a purification-mode algorithm. E/nestin:lacz transfected cells were used as a control to set the background fluorescence; a false positive rate of 0.1-0.3% was accepted to ensure adequate yield. E/nestin:EGFP and p/Tα1:hGFP-transfected cells were sorted at a rate of 1000-3000 cells/second. GFP+ cells were then plated onto laminin-coated 24-well plates, in DMEM/F12/N2 with 5% FBS and BrdU. At 2 and 7 days post-FACS, the sorted cultures were fixed and stained for BrdU together with either TuJ1/βIII tubulin or MAP-2; selected plates were also stained for O4 or GFAP as described (Roy et al., 1999).

Data Analysis

Experimental endpoints included the proportion of cells expressing each antigenic marker (all nominally GFP+ following sorting), as a function of time after FACS. At each sampled time-point, the proportions of neurons were compared to those of unsorted controls that were similarly dispersed, but replated without sorting, after adjusting their concentration to that of the sorted pool after FACS. For each combination of treatment (sorted or unsorted) and immunolabeling, the number of stained and unstained cells were counted in 10 randomly chosen fields, in each of 3 triplicate cultures.

Calcium Imaging

To identify neurons physiologically, selected fields were challenged with a depolarizing stimulus of 60 mM potassium, during which their cytosolic calcium levels were observed. Calcium imaging was performed using confocal microscopy of cultures loaded with fluo-3 acetoxymethylester (fluo-3, Molecular Probes, Eugene, Oreg.), as described (Pincus et al., 1998b; Kirschenbaum et al., 1994). A Bio-Rad MRC600 confocal scanning microscope, equipped with an argon laser and coupled to a Nikon Diaphot 300 microscope, was used to image the fluo-3 signal. These neurons show a mean calcium increase of more than 400% to 60 mM potassium in vitro; this is in contrast to an astrocytic calcium response of less than 20%, and undetectable oligodendroglial responses (Kirschenbaum et al., 1994). Thus, neuronal identity was assigned to cells exhibiting $\geq$3-fold calcium increments to depolarization.

Electrophysiology

P/Tα1:GFP+ fluorescent neurons were first imaged using Imaging Workbench (Axon Instruments, Inc., Burlington, Calif.). Excitation was provided by 480 nm monochromated light (DeltaSCAN-1, PTI). Emission was low-pass filtered (515 nm). An intensified CCD video camera (IC-100, PTI, South Brunswick, N.J.) coupled to an Olympus B×50 microscope was used to obtain images. Whole-cell voltage-clamped recordings (Kang et al., 1998) were then made of the labeled neurons, under differential inference contrast (DIC) optics at 23-24° C. Patch electrodes with a resistance of 4-7 MΩ were pulled from KG-33 glass capillaries (inside diameter, 1.0 mm, outside diameter, 1.5 mm, Garner Glass, Claremont, Calif.), using a P-97 electrode puller (Sutter Instrument, Novato, Calif.). Any seal resistance less than 5GΩ were rejected. The pipette solution contained 120 mM K-gluconate, 10 mM KCl, 1 mM $MgCl_2$, 10 mM HEPES, 0.1 mM EGTA, 0.025 mM $CaCl_2$, 1 mM ATP, 0.2 mM GTP, and 4 mM glucose (pH 7.2). The extracellular solution contained 130 mM NaCl, 3 mM KCl, 1.25 mM $NaH_2PO_4$, 2 mM $MgCl_2$, 2 mM $CaCl_2$, and 10 mM glucose. A holding potential of −60 mV and voltage steps of 10 mV with 100-ms durations were applied to the recorded cells through the patch electrodes. Recordings were made using Axopatch 200B and PCLAMP 7.0. The software was used to subtract capacitative and/or linear leak currents. Signals were sampled every 50 μs. Data were further processed with Origin 4.1 (Microcal, Northhampton, Mass.) and CorelDraw 7.0 (Corel, Ontario, Canada).

Example 2

Neurons can be Harvested in High-Yield from the Adult Human Dentate Gyrus

To characterize mitotic cell types harvestable from the adult human hippocampus, papain dissociates of surgically-resected hippocampus were obtained from eight patients. All were males, ranging from 5 to 63 years old. Four patients had temporal lobe resections for medication-refractory epilepsy (Pincus et al., 1998b); two were subjected to decompressive resection during or after extra-axial meningioma removal, one sample was taken during aneurysm repair, and one during decompression for traumatic edema. In each, the dentate gyrus was dissected free of the temporal ventricular zone, and the two removed separately. The dentate was dissociated using papain/Dnase (Palmer et al., 1997); the resultant cultures were raised in DMEM/F12/N2, with 20 ng/ml FGF2 and 2% platelet-depleted fetal bovine sera (PD-FBS). A mitotic marker, bromodeoxyuridine (BrdU; 10 μg/ml) was added at 6 hours in vitro. Cultures were fixed at 1, 2, or 4 weeks in vitro, and their resident phenotypes assessed by immunolabeling for one of two neuron-selective proteins, βIII-tubulin/TuJ1 (Lee et al., 1990; Menezes et al., 1994) or MAP-2 (Bernhardt et al., 1984).

Among randomly-chosen low-power fields of dissociated hippocampus (10/patient), 14.5±6.8% of the scored cells expressed βIII-tubulin/TuJ1-immunoreactivity at 1 week in culture (mean±SEM; n=3 patients) (FIGS. 2A-F). At this time-point, MAP-2, which appears later in neuronal development than TuJ1, was expressed by 2.3±1.3% of the hippocampal cells. By 30 days in vitro (DIV), the percentage of MAP-2+ cells in each plate rose to 6.13±1.4%, and that of TuJ1+ cells to 14.9±7.8%. The relatively high initial incidence of cells expressing βIII-tubulin, which appears early in neuronal ontogeny, together with the later maturation of MAP-2+ cells, suggested that these neurons arose from precursors, rather than from resident neurons that survived dissociation. The high proportion of TuJ1+ cells that incorporated BrdU (see below), indicating their mitogenesis in vitro, confirmed this point.

Example 3

Persistent Neurogenesis by Mitotic Progenitors in Adult Hippocampal Cultures

A substantial proportion of the antigenically-confirmed neurons incorporated BrdU from the culture media, indicating their genesis in vitro (FIGS. 2A-F). BrdU⁺/βIII-tubulin⁺ neurons constituted 25.4±5.9% of all βIII-tubulin-defined neurons at 7 DIV. At this same time, BrdU⁺/MAP-2⁺ cells were rare, consistent with the relatively late appearance of MAP-2 after neuronal mitogenesis. But by 14 DIV, 3.0±1.0% of all cells in these cultures expressed MAP-2, and of these, 22.5±7.3% were BrdU⁺.

The persistence of neurogenesis in these dissociates was also manifested by the sustained neuronal incorporation of BrdU in cultures to which the marker was first added after five days in culture. Among plates first exposed to BrdU on day 5 in vitro and fixed on day 7, 8.2±1.9% of the cells expressed TuJ1; this was roughly identical to the 8.9±2.8% incidence of TuJ1⁺ neurons in the plates exposed to BrdU from the outset (n=10 fields/sample). Importantly, among those TuJ1⁺ neurons scored in the late BrdU-addition plates, 13.2±7.6% co-labeled with BrdU when fixed at 7 DIV. Thus, new hippocampal neurons continued to be generated for at least the first week in culture. Moreover, neurogenesis was sustained beyond the first week, as reflected in an increasing number of neurons as a function of time in vitro. Among a sample of hippocampal cultures fixed at serial timepoints after plating, the average numbers of βIII-tubulin/TuJ1⁺ and total cells/field rose from 2.0±0.2 and 23.6±1.0, respectively, at 7 DIV (n=141 low-power fields), to 10.3±0.7 TuJ1⁺ and 136.4±7.1 total cells/field at 30 DIV (n=142). Yet despite this 5-fold increase in the number of neurons/field over the month in vitro, the commensurate increase in total cell number insured that the net percentage of TuJ1-defined neurons in these cultures was constant: 6.7±0.6% at 7 DIV, and 8.9±1.1% at 30 DIV. Together, these data indicated that neurons could be generated from dividing progenitors in cultures of the adult human hippocampus.

Example 4

The Tα1 Tubulin Promoter Identifies Immature Neurons and Mitotic Neuronal Progenitors in Adult Hippocampal Cultures To identify and separate neuronal progenitors from the adult hippocampus, mixed cell dissociates were transfected with plasmid DNA bearing fluorescent transgenes placed under the control of cell-specific promoters; the cell types of interest fluoresced, and may thereby be isolated by FACS. To establish the feasibility of this strategy for selecting progenitor cells from the CNS, a separation vector was constructed by placing the gene encoding humanized green fluorescence protein (GFP) (Chalfie et al., 1994) under the control of the Tα1 tubulin promoter (P/Tα1), an early neuronal regulatory sequence (Miller et al., 1987; Gloster et al., 1994). The resultant plasmid P/Tα1:hGFP was transfected into dissociated forebrain cultures, and it was observed that P/Tα1:hGFP was strongly expressed by precursors and very young neurons, but not by glia (Wang et al., 1998b). This allowed the use of FACS to enrich the transfected progenitors, based upon their P/Tα1 tubulin-driven GFP fluorescence. By this strategy, it was possible to identify and select neuronal precursor cells from both the fetal and adult rat brain (Wang et al., 1998b). As described herein, this strategy was extended to enrich neuronal progenitors from the adult human brain, by sorting cells obtained from the adult hippocampus after transfection with pP/Tα1:hGFP.

Before attempting to isolate adult hippocampal progenitor cells, it was first necessary to establish that P/Tα1:hGFP could indeed identify them. Four adult hippocampi were used for this purpose; these included resections derived from 5, 20, 33, and 50 year-old male patients. All were dissociated and plated, and randomly selected plates were transfected on day 1 in vitro with P/Tα1:hGFP plasmid DNA. Within 4 days after transfection, a discrete population of fiber-bearing, initially bipolar cells was noted to express GFP (FIGS. 3A-F). These cells expressed neuronal βIII-tubulin, and matured to express MAP-2 over the first 10 DIV. The P/Tα1:hGFP⁺ cells failed to express either glial fibrillary acidic protein (GFAP) or oligodendrocytic O4, supporting the neuronal specificity of the P/Tα1:hGFP selection cassette. Furthermore, the P/Tα1:hGFP⁺ cells included mitotically generated neurons; both BrdU⁺ and BrdU⁻ Tα1:hGFP⁺ cells were confirmed as neuronal by their co-expression of βIII-tubulin (FIGS. 6A-D, below).

Example 5

The Nestin Enhancer also Identifies Immature Neurons and Mitotic Progenitors in the Adult Hippocampus To identify potentially less-committed neural progenitor cells of the adult human hippocampus, an expression vector encoding GFP placed under the control of the nestin enhancer, comprised of the 2nd intron of the nestin gene (Zimmerman et al., 1994), was used. The 637 bp-region between bases 1162 and 1798 of the rat nestin gene is sufficient to target gene expression to neuroepithelial progenitor cells (Lothian et al., 1997) and is conserved between rats and humans. It was placed upstream of the minimum promoter of heat shock protein-68 (Rossant et al., 1991), a sequence that exhibits no basal activity unless an enhancer is placed in its vicinity; the resultant E/nestin:P/hsp68 construct was ligated to EGFP-polyA to yield the selection plasmid, E/nestin:EGFP. The neural progenitor cell-specific expression of this transgene has been confirmed in transgenic mice.

This E/nestin:EGFP construct recognized a relatively primitive population of initially flat and bipolar hippocampal cells, that constituted 0.53±0.20% of the scored cells (n=30 scored fields, 10 each from 3 patients). These cells were typically nestin⁺/TuJ1±/GFAP⁻/O4⁻ at 1 DIV. In the week after transfection, 62.5±2.9% of the E/nestin:EGFP cells developed TuJ1-immunoreactivity. Among these, 21.0±15.2% incorporated BrdU during that week, indicating both their progression from a nestin to βIII-tubulin⁺ neuronal phenotype, and their mitogenesis in vitro (FIGS. 4A-I). Almost a third of the E/nestin:EGFP⁺ cells remained morphologically undistinguished. Of these, a small number developed into GFAP⁺ astrocytes, but under conditions which included 2% PD-FBS in DMEM/F12/N2, virtually all of the remainder continued to express nestin protein. Thus, E/nestin:EGFP identified adult hippocampal cells that were mitotically competent and able to generate new neurons. They appeared to comprise a neuronal progenitor population analogous, if not identical, to the P/Tα1:hGFP-defined hippocampal cell pool.

Example 6

FACS Based on Tα1:hGFP May be Used to Select and Enrich Neuronal Progenitor Cells from the Adult Hippocampus Using fluorescence-activated cell sorting, P/Tα1:hGFP⁺ hippocampal cells were next isolated and enriched to purity, from 1 ml aliquots of dentate dissociates prepared from each of 4 patients (FIG. 1). Manual counts of these cells on a hemocytometer yielded an average of 197,500±72,169 dentate cells/sorted sample, whereas flow cytometry yielded 402,634±205,833 cells/sample (all values given as mean±SEM). The larger number obtained through flow cytometry likely included damaged cells and free nuclei, even after gating to avoid debris. The hemocytometer counts, in contrast, were limited to viable cells, as assessed morphologically and confirmed by trypan blue exclusion.

Figure 7:
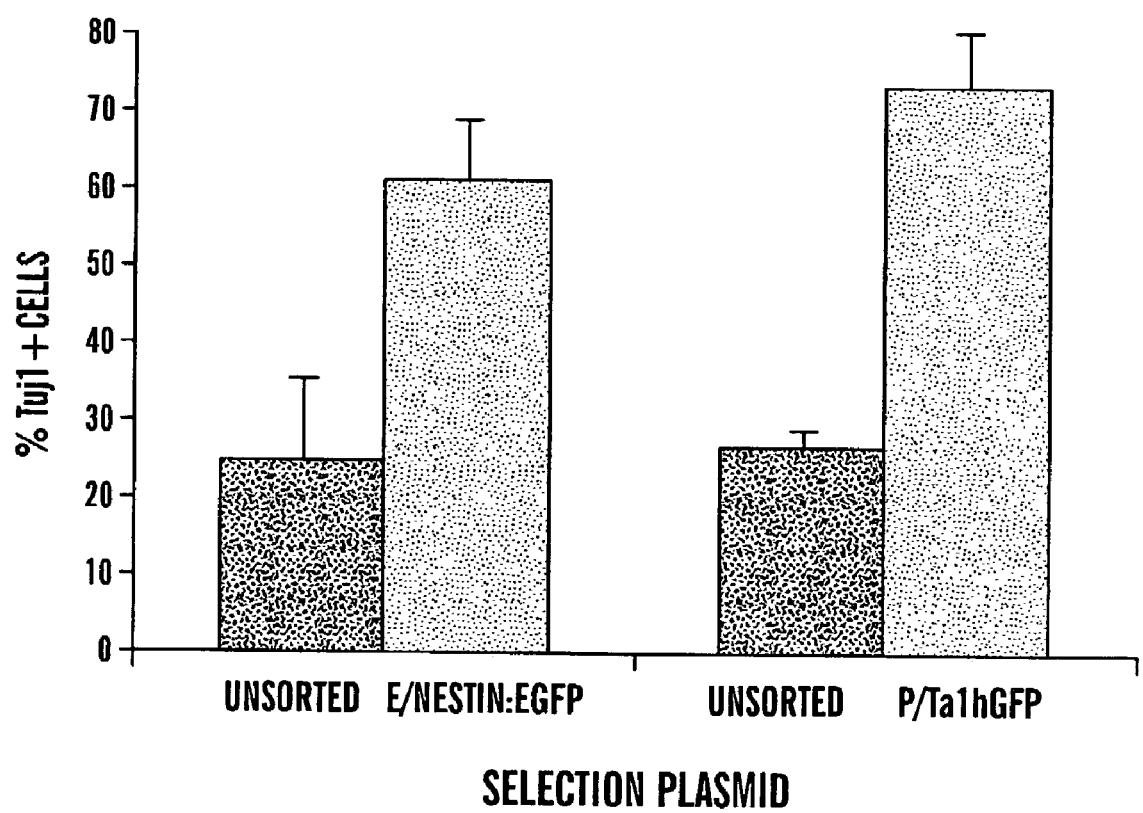
FIG. 7 is a graph showing that P/Tα1:hGFP-based and E/nestin:EGFP-based FACS each enriched neuronal progenitor cells from the adult hippocampus. Using stringent FACS criteria intended for cell-type purification, the percentage of TuJ1⁺ cells increased from 26.9±1.9% in unsorted cultures to 73.2±6.6% by a week after P/Tα1:hGFP-based FACS (n=3 runs), and from 24.8±10.9 to 61.0±7.6% following E/nestin:EGFP-based FACS. Each sort yielded significant enrichment of TuJ1⁺ cells (p<0.01 after Boneferroni adjustment). Essentially all of the P/Tα1:hGFP⁺/TuJ1⁻ cells, and most of their E/nestin:EGFP⁺/TuJ1⁻ counterparts, expressed nestin protein.
Figure 8A:
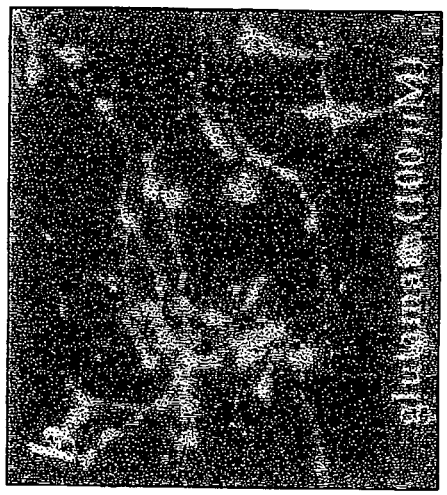
FIGS. 8A-F show that P/Tα1:hGFP-sorted hippocampal cells developed into physiologically mature neurons.
Figure 8B:
Figure 8C:
Figure 8D:
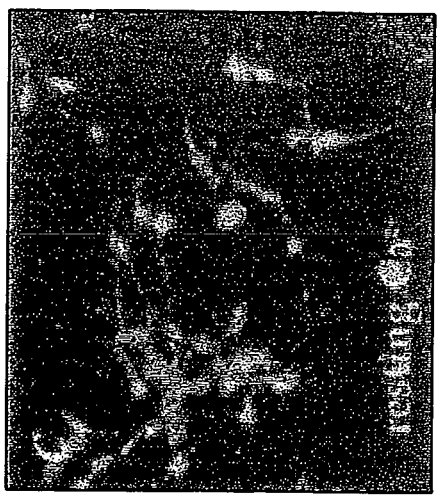
Figure 8E:
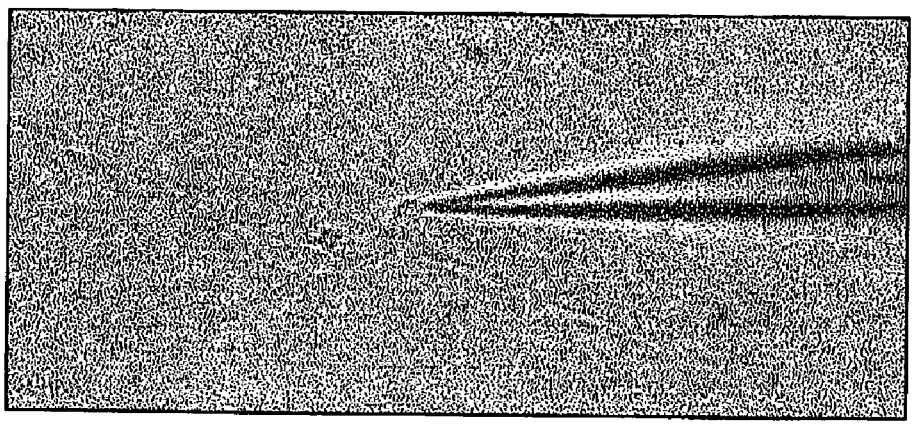
Figure 8F:
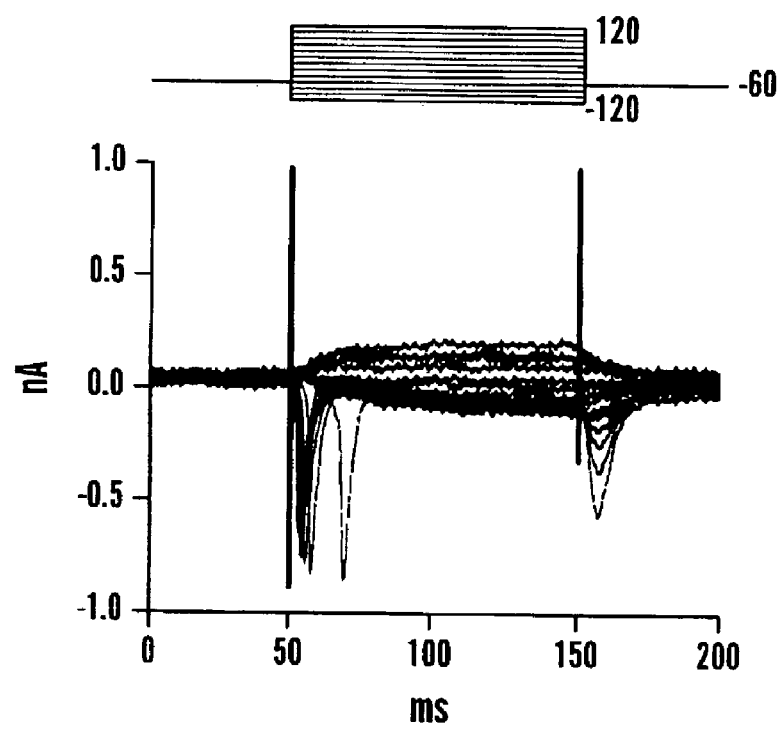

Of the P/Tα1:hGFP-transfected samples, an average of 3324±1113 cells were scored as GFP$^+$ by FACS; given the high stringency cut-off for fluorescence assignment that was used, essentially all of these could be confirmed visually as expressing GFP. Thus, the P/Tα1:hGFP$^+$ isolates effectively included 1.11±0.35% of the hemocytometer-scored cell population (FIGS. 5A-H). Within the weeks after FACS, these P/Tα1:hGFP-sorted cells matured into morphologically and antigenically characteristic neurons (FIGS. 6A-D). One week after FACS, both the sorted plates and their unsorted controls were switched from base media containing 2% PD-FBS and 10 ng/ml FGF2, in which they were raised initially to allow progenitor division, to 5% FBS and 20 ng/ml BDNF, to encourage neuronal differentiation and survival (Pincus et al., 1998b). Fully 73.2±6.6% of the sorted cells expressed βIII-tubulin immunoreactivity a week after FACS, while only 14.5±6.8% and 26.9±1.9% of the cells in the unsorted dissociates did so at 7 and 14 DIV, respectively. Each of these comparisons yielded a significant increment in βIII-tubulin/TuJ1$^+$ cells as a result of P/Tα1:hGFP-based FACS (p<0.01 by one-way ANOVA with Boneferroni adjustment) (FIG. 7). Among the sorted βIII-tubulin$^+$ cells, 19.1±0.2% incorporated BrdU during their initial week in low-serum, FGF2-supplemented culture, indicating that P/Tα1:hGFP-sorted adult dentate cells were still mitotically competent. Furthermore, of the TuJ1$^-$ cells in the sorted pool, essentially all expressed nestin protein, and did not otherwise develop a differentiated phenotype in the week after FACS.

Example 7

FACS Based on Nestin:EGFP May be Used to Select and Enrich Neural Progenitor Cells from the Adult Hippocampus FACS was next used to isolate E/nestin:EGFP$^+$ cells from both juvenile and adult hippocampal dissociates, again using samples dissected free of their overlying ventricular epithelium (n=3 male patients: 5, 33 and 50 years old). As a result, the largely nestin$^+$ ependymal/subependymal pool of the ventricular zone would not have been present in these samples. The target population of the E/nestin:EGFP plasmid was instead intended to be the nestin$^+$ cells of the adult human dentate gyrus, which was postulated would include neural precursors as in its rodent counterpart (Palmer et al., 1997).

Using 1 ml dissociates of adult dentate gyrus, an average of 405,768±209,852 cells were counted as single events by the sorter in purification mode. Of 273,333±156,950 hemocytometer-confirmed viable dentate cells/sorted sample, 11,331±10,737, or 1.96±1.26%, were gated in purification mode as E/nestin:GFP$^+$ cells (FIGS. 5A-H). These E/nestin:EGFP$^+$-sorted cells initially expressed nestin protein ubiquitously. Within the week after FACS, though, 61.0±7.6% of the E/nestin-sorted pool developed βIII-tubulin immunoreactivity, while only 24.8±10.9% of the cells in unsorted controls expressed III-tubulin at that point (p<0.01 by Student's t test) (FIG. 7). In the 5% FBS/BDNF environrment to which the cells were switched after FACS, most of the E/nestin:EGFP$^+$-sorted cells that were TuJ1$^-$ continued to express nestin; only uncommon glia were noted in the sorted pool, even at a week after FACS. Among the E/nestin:EGFP-sorted TuJ1$^+$ cells, 21.7±3.3% incorporated BrdU during their first week in culture. Thus, like their Tα1:hGFP-separated counterparts, the E/nestin:EGFP-sorted cells matured as neurons in the weeks after FACS.

Example 8

Progenitor-Derived Hippocampal Neurons Developed Neuronal Calcium Responses to Glutamate and Depolarization-Induced Calcium Increments To establish the ability of newly generated adult hippocampal cells to respond in a neuronal fashion to depolarizing stimuli, selected cultures (n=4, derived from 2 brains) were loaded with the calcium indicator dye fluo-3, and exposed to 60 mM potassium during confocal microscopy. Astrocytic responses to depolarization were minimal under these culture conditions, as previously noted (Kirschenbaum et al., 1994). In contrast, neuron-like cells verified as such displayed rapid, reversible elevations in cytosolic calcium in response to potassium, consistent with the activity of neuronal voltage-gated calcium channels (Zimmerman et al., 1994; Kirschenbaum et al., 1994) (FIGS. 8A-F). The neuronal phenotype of these cells was then validated antigenically, by immunostaining for βIII-tubulin. Further immunolabeling revealed that a distinct subpopulation of these βIII-tubulin$^+$ cells had incorporated BrdU, indicating their in vitro mitogenesis.

Example 9

Progenitor-Derived Hippocampal Neurons Developed Voltage-Gated Sodium Channels

To assess the development of neuronal fast sodium currents by P/Tα1:hGFP-defined progenitor-derived neurons, hippocampal cultures (n=3, from 2 patients) were transfected with P/Tα1:hGFP, and the GFP$^+$ cells then assessed by whole-cell patch clamp recording. P/Tα1:hGFP$^+$ cells were identified by their persistent fluorescence, then patch-clamped, and recorded in a voltage-clamped configuration during current stimulation (FIGS. 8A-F). Voltage-activated Na$^+$ currents, which form the ionic basis of the neuronal action potential, were found in each of 4 P/Tα1:hGFP$^+$ cells recorded. In these, the maximal $I_{Na}$ was 617±136 (n=4). In contrast, none of 13 non-fluorescent cells recorded in these unsorted cultures, which included a variety of glial morphologies, displayed significant current-induced sodium current. In this regard, although voltage-gated Na$^+$ channels have been found in glia (Sontheimer et al., 1991; Sontheimer et al., 1992), hippocampal astrocytes do not express these channels in sufficient numbers to mediate the fast sodium currents of neuronal depolarization (Tse et al., 1992; Kang et al., 1998).

Example 10

Human Hippocampal Neural Progenitor Cells

The results as described in Examples 2-9 indicate that the adult human hippocampus harbors mitotically competent progenitor cells, that can give rise to new neurons. These findings extend a recent report of hippocampal neurogenesis in tissue sections of adult human brain (Eriksson et al., 1998), both by identifying viable hippocampal progenitor cells, and by establishing a means for their specific extraction in a manner that allows their physiologically-appropriate maturation. By transfecting hippocampal dissociates with plasmid DNA encoding GFP expressed under the control of two early neural regulatory sequences, the nestin enhancer and the Tα1 tubulin promoter, it was possible to identify and sort neuronal progenitors from the native adult human hippocampus, in substantial numbers and purity. These cells remained mitotically-competent after FACS and matured as functionally-competent neurons. This appears to be the first reported targeted selection and extraction of mitotically-competent neuronal progenitor cells from any nonventricular region of the adult human brain or spinal cord.

The P/Tα1:hGFP and E/nestin:EGFP-based sorts produced similar results, and yielded a surprising abundance of both phenotypes, even under high-stringency sort conditions. The average transfection efficiency of 9.40±0.9% (see Example 1) suggests that the cytometric yields of P/Tα1:GFP and E/nestin:EGFP-defined progenitors, 1.11±0.35% and 1.96±1.26%, respectively, may reflect much larger pools of potentially neurogenic cells in the adult human dentate gyrus. These estimates are substantially higher than the incidence of human hippocampal neurogenesis inferred from histological sections (Eriksson et al., 1998), suggesting that the dentate gyrus harbors a relatively large pool of mitotically quiescent progenitor cells. However, these numbers may include dentate cells capable of resuming an early neuronal transcriptional program when removed to a permissive culture environment, without cell cycle re-entry; these may exceed the actual number of dentate progenitor cells that can divide to give rise to new neurons in vivo.

Although nestin and Tα1 tubulin are expressed at different stages in neuronal ontogeny—nestin by uncommitted as well as phenotype-restricted progenitors (Frederiksen et al., 1988; Lendahl et al., 1990), and Tα1 tubulin by their neuronally-restricted daughters (Gloster et al., 1994)—their promoters appeared to recognize largely overlapping cell types in the adult hippocampus. Yet this is not surprising in the relatively homogeneous cell environment of the dentate gyrus: the astrocytic complement of the dentate is minor, and oligodendrocytes are scarce in the granular layer. As a result, the nestin gene may be transcribed by roughly the same pool of granule cell neuronal progenitors in the adult hippocampus as the Tα1 tubulin gene.

The typical fate of E/nestin-defined hippocampal cells was neuronal under these conditions. Nonetheless, both neuronally-committed and multipotent progenitors may be recognized by E/nestin:EGFP (Lendahl et al., 1990). No attempt was made at further lineage analysis of the E/nestin:EGFP+ cells, or of assessing their clonal derivatives, since the principal purpose in the above examples was to isolate neuronal progenitors from the adult hippocampus; that some of these may have been persistent neural stem cells remains a distinct possibility (Palmer et al., 1997; McKay, 1997), that begs further study of the lineage potential and self-renewability of these cells.

The therapeutic implications of adult hippocampal neurogenesis may be profound. The existence of a mitotic progenitor pool in the human dentate suggests that neuronal recruitment to this pool might be modulated pharmacologically or experientially in adulthood, as in rodent models (Gould et al., 1998; Kempermann et al., 1997; van Praag et al., 1999). Just as learning is associated with increased hippocampal neurogenesis in rodents (Gould et al., 1999), the targeted induction or supplementation of this progenitor pool might directly influence learning and memory in humans. The ability to target and extract adult hippocampal progenitor cells in significant numbers should permit hitherto unapproachable studies of their mitotic capacity, growth control, maturation competence, and engraftability. These studies in turn should provide new insights into the function of these cells in the normal adult human, their potential for exogenous activation and induced neurogenesis, and their utility as agents for hippocampal reorganization and repair.

Although preferred embodiments have been depicted and described in detail herein, it will be apparent to those skilled in the relevant art that various modifications, additions, substitutions and the like can be made without departing from the spirit of the invention and these are therefore considered to be within the cope of the invention as defined in the claims which follow.

LIST OF REFERENCES CITED

The following is a list of references cited in this application. All of these citations are hereby incorporated by reference.

Altman, J., et al., *J. Comparative Neurology* 124:319-335 (1965).
Barami, K., et al., *J Neurobiol* 28:82-101 (1995).
Barnea, A. et al., *Proc. Natl. Acad. Sci.* 91:11217-11221 (1994).
Bayer, S., et al., *Science* 216:890-892 (1982).
Bernhardt, R., et al., *J Comp Neurol* 226:203-221 (1984).
Chalfie, M., et al., *Science* 263:802-805 (1994).
Doetsch, F., et al., *Cell* 97:703-716 (1999).
Eriksson, P., et al., *Nature Med* 4:1313-1317 (1998).
Frederiksen, K., et al., *J Neurosci* 8:1144-51 (1988).
Gage, F., et al., *Ann Rev Neurosci* 18:159-192 (1995a).
Gage, F., et al., *Proc Natl Acad Sci USA* 92:11879-11883 (1995b).
Gloster, A., et al., *J. Neuroscience* 14:7319-7330 (1994).
Goldman and Luskin, *Trends in Neurosci.* 21(3):107-14 (1998).
Goldman, *J. Neurobiol.* 36:267-86 (1998).
Goldman, et al., *J. Neurobiol.* 30(4):505-20 (1996).
Goldman, S., *J. Neurosci* 10:2931-2939 (1990).
Goldman, S., *The Neuroscientist* 1:338-350 (1995).
Goldman, S., In: *Isolation, characterization and utilization of CNS stem cells*. F. Gage, Y. Christen, eds., Foundation IPSEN Symposia. Springer-Verland, Berlin, p. 43-65 (1997).
Goldman, S., and Nedergaard, M., *Dev Brain Res* 68:217-223 (1992).
Goldman, S., and Nottebohm, F., *Proc Natl Acad Sci USA* 80:2390-2394 (1983).
Gould, E., et al., *J. Neuroscience* 17:2492-2498 (1997).
Gould, E., et al., *Proc. Natl. Acad. Sci.* 95:3168-3171 (1998).
Gould, E., et al., *J. Neurosci.* 12:3642-3650 (1992).
Gould, E., et al., *Nature Neurosci.* 2:260-265 (1999).
Kang, J., et al., *Nature Neurosci* 1:683-692 (1998).
Kaplan, M. S., et al., *Science* 197:1092-1094 (1977).
Kempermann, G., et al., *Nature* 386:493-495 (1997).
Kilpatrick, T., and Bartlett, P., *J Neurosci* 15:3563-3661 (1995).
Kirschenbaum, B., et al., *Cerebral Cortex* 4:576-589 (1994).
Kirschenbaum, B., and Goldman, S., *Soc Neurosci Abstr* 317.8 (1995b).
Kirschenbaum, B., and Goldman, S., *Proc Natl Acad Sci USA* 92:210-214 (1995a).
Kornack, D., et al., *Proc. Natl. Acad. Sci.* 96:5768-5773 (1999).
Korr, H., *Adv Anat Embryol Cell Biol* 61:1-72 (1980).
Kuhn, et al., *J. Neurosci.* 17(15):5820-29 (1997).
Kukekov, V., et al., *Exp. Neurol.* 156:333-344 (1999).

Lee, M., et al., *Proc. Natl. Acad. Sci.* 87:7195-7199 (1990).
Lendahl, U., et al., *Cell* 60:585-595 (1990).
Levy, J., et al., *Nature Biotech* 14:610-614 (1996).
Lois, C., and Alvarez-Buylla, A., *Proc Natl Acad Sci USA* 90:2074-2077 (1993).
Lothian C., et al., *Eur J Neurosci* 9:452-462 (1997).
McKay, R., *Science* 276:66-71 (1997).
Menezes, et al., *J.Neurosci.* 14(9):5399-416 (1994).
Miller, F., et al., *J. Cell Biology* 105:3065-3073 (1987).
Morshead, C., et al., *Neuron* 13:1071-1082 (1994).
Palmer, T., et al., *Mol Cell Neurosci* 8:389-404 (1997).
Palmer, T., et al., *Mol Cell Neurosci* 6:474-486 (1995).
Pincus, et al., *Neurosurgery* 42:858-68 (1998a).
Pincus, D. W., et al., *Ann Neurol.* 43:576-85 (1998b).
Reynolds, B., and Weiss, S., *Science* 255:1707-1710 (1992).
Richards, L., et al., *Proc Natl Acad Sci USA* 89:8591-8595 (1992).
Rossant, J., et al., *Genes Dev* 5:1333-44 (1991).
Roy, N., et al., *J Neurosci* 19:9986-9995 (1999).
Sambrook et al., *Molecular Cloning: A Laboratory Manual*, 2d Edition, Cold Spring Harbor Laboratory Press, Cold Spring Harbor, N.Y. (1989).
Sontheimer, H., et al., *J. Neurosci. Res.* 30:275-287 (1991).
Sontheimer, H., et al., *J. Neurophysiol.* 68:985-1000 (1992).
Sturrock, R., *Adv Cell Neurobiol*, vol. 3, Academic Press, New York, p. 1-33 (1982).
Suhonen, J., et al., *Nature* 383:624-627 (1996).
Tse, F. W., et al., *J. Neuroscience* 12:1781-1788 (1992).
van Praag, H., et al., *Nature Neurosci.* 2:266-270 (1999).
Vescovi, A., et al., *Neuron* 11:951-966 (1993).
Wang, et al., *Ann. Neurol.* 44:438 (1998a).
Wang, S., et al., *Nature Biotechnology* 16:196-201 (1998b).
Zappone et al., *Development* 127:2367-2382 (2000).
Zimmerman, et al., *Neuron* 12:11-24 (1994).

What is claimed:

1. An enriched or purified preparation of unpassaged neuronally restricted progenitor cells solely derived from the dentate gyrus of the adult human hippocampus.

2. The enriched or purified preparation according to claim 1, wherein the neuronally restricted progenitor cells are immortalized.

3. The enriched or purified preparation according to claim 2, wherein the neuronally restricted progenitor cells are immortalized with a transforming oncogene.

4. The enriched or purified preparation according to claim 1, wherein the neuronally restricted progenitor cells are transduced with an exogenous transgene.

5. The enriched or purified preparation according to claim 1, wherein the neuronally restricted progenitor cells maintain mitotic competence in culture.

6. The enriched or purified preparation according to claim 1, wherein the neuronally restricted progenitor cells are capable of maturing into functionally competent neurons.

* * * * *